United States Patent

Hong, II et al.

Patent Number: 6,040,337
Date of Patent: Mar. 21, 2000

[54] 5-DEMETHOXYFUMAGILLOL DERIVATIVES AND PROCESSES FOR PREPARING THE SAME

[75] Inventors: Chung Hong, II, East Amherst, N.Y.; Jung Woo Kim, Seoul, Rep. of Korea; Sang Joon Lee, Kyunggi-do, Rep. of Korea; Soon Kil Ahn, Seoul, Rep. of Korea; Nam Song Choi, Seoul, Rep. of Korea; Ryung Kee Hong, Seoul, Rep. of Korea; Hyoung Sik Chun, Seoul, Rep. of Korea; Seung Kee Moon, Seoul, Rep. of Korea; Hong Woo Lee, Kyunggi, Rep. of Korea

[73] Assignee: Chong Kun Dang Corporation, Seoul, Rep. of Korea

[21] Appl. No.: 09/311,777

[22] Filed: May 13, 1999

[30] Foreign Application Priority Data

May 15, 1998 [KR] Rep. of Korea .................. 98-17637

[51] Int. Cl.⁷ .................. A61K 31/335; C07D 301/32; C07D 303/08
[52] U.S. Cl. .................. 514/475; 549/512; 549/541
[58] Field of Search .................. 514/475; 549/512, 549/541

[56] References Cited

FOREIGN PATENT DOCUMENTS 0 354 787 A1  2/1990  European Pat. Off. .................. 303/16
0 415 294 A2  3/1991  European Pat. Off. .................. 303/22

OTHER PUBLICATIONS

Tarbell, D. S., et al., "The Chemistry of Fumagillin," *J. Amer. Chem. Soc.*, 83:3096–3113 (1961).

Marui, S. and Kishimoto, S., "Chemical Modification of Fumagillin. II. 6–Amino–6–deoxyfumagillol and Its Derivatives," *Chem. Pharm. Bull.*, 40:575–579 (1992).

Marui et al., "Chemical Modification of Fumagillin. I. 6–O–Acyl, 6–O–Sulfonyl, 6–O–Alkyl, and 6–O–(N–Substituted–carbamoyl)fumagillols," *Chem. Pharm. Bull.*, 40:96–101 (1992).

Billington, David C., "Angiogenesis and Its Inhibition: Potential New Therapies In Oncology and Non–Neoplastic Diseases," *Drug Design and Discovery*, 8:3–35 (1991).

Molander, G.A., and Hahn, G., "Lanthanides in Organic Synthesis. 2. Reduction of α–Heterosubstituted Ketones," *J. Org. Chem.*, 51:1135–1138 (1986).

Hanson, F. R. and Eble, T. E., "An Antiphage Agent Isolated from *Aspergillus Sp.*," *J. Bact.*, 58:527–529 (1949).

*Primary Examiner*—Johann Richter
*Assistant Examiner*—Taofiq A. Solola
*Attorney, Agent, or Firm*—Heslin & Rothenberg, P.C.

[57] ABSTRACT

Compounds useful as angiogenesis inhibiting agents and processes for their preparation are disclosed. In one embodiment, the compounds of the invention are represented by Formula 1:

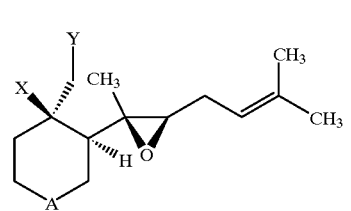

Also disclosed is a pharmaceutical composition for inhibiting angiogenesis in a mammal, said composition comprising a compound of Formula 1, or a pharmaceutically acceptable salt thereof, as an active ingredient.

6 Claims, No Drawings

5-DEMETHOXYFUMAGILLOL DERIVATIVES AND PROCESSES FOR PREPARING THE SAME

CLAIM FOR FOREIGN PRIORITY

This application claims the priority of Korean Patent Application No. 1998-17637, filed May 15, 1998.

TECHNICAL FIELD

The present invention relates to a novel 5-demethoxyfumagillol derivative or a pharmaceutically acceptable salt thereof which exhibits excellent angiogenesis inhibiting activities, to a process for preparing the same and to a pharmaceutical composition comprising the same as an active ingredient.

BACKGROUND OF THE INVENTION

Angiogenesis is a phenomenon of generating a new capillary vessel, which is a normal physiological function, as well as a pathological function caused by various diseases. Angiogenesis has a deep connection with growth and transfer of solid cancer, rheumatic arthritis, diabetic retinopathy, psoriasis, or the like [Billington, D.C., *Drug Design and Discovery*, 8:3–35 (19910]. In 1971, Judah Folkman of the Medical College of Harvard University, USA, suggested a novel concept of treating solid cancer by inhibiting angiogenesis. [Folkman, J., *New Eng. Med.*, 185:1182 (1971)].

Recently, the clinical importance of therapeutic agents as a means of controlling angiogenesis has been emphasized, and various researches on angiogenesis have been performed. According to clinical results of anticancer medicines using angiogenesis inhibitors, in particular, it is expected that they cause little problems caused by general anticancer medicines, including adverse effect and tolerance. In other words, an angiogenesis inhibitor does not directly act on tumor cells, but acts on endothelial cells of a living organism, and thus, the problem of tolerance does not probably occur, and a synergistic anticancer effect is expected by a therapy in combination with conventional anticancer medicines which have been employed up to the present.

Various fumagillin compounds inhibiting angiogenesis have been reported. For example, it is known that fumagillin having angiogenesis inhibiting action is produced by culturing *Aspergillus fumigatus*, a productive strain isolated from a soil sample. [Eble, T. E., Hanson, F. R.

Antibiotics & chemotherapy, 1, 54 (1951), Eble, T. E., Hanson, F. R. J.

Bact., 58, 527 (1949)] [Ingber, G., Fujita, T., Kishimoto, S., Sudo, K., Kanmaru, T., Bre, H., Folkman, J., Nature 248, 555(1990)]

Besides, EP-A-354787, EP-A-357061, JP-A01-233275 and EP-A-415294 have been disclosed; and 6-amino-6-deoxy fumagillol [Chem. Pharm. Bull., (1992), 40, 575], 6-acyl, 6-O-sulfonyl, 6-O-alkyl and 6-O-(N-substituted carbamoyl) fumagillol [Chem. Pharm. Bull., (1992), 40, to 96] are reported to have angiogenesis inhibiting action. However, continuous development of angiogenesis inhibitors having less toxicity and more excellent effect is further required.

DISCLOSURE OF THE INVENTION

The present inventors have performed intensive studies to solve the problems described above, and, as a result, developed novel 5-demethoxyfumagillol derivatives derived from 5-demethoxyfumagillol, and completed the invention.

The object of the present invention is to provide 5-demethoxyfumagillol derivatives represented by Chemical Formula 1.

Another object of the present invention is to provide a process for preparing a 5-demethoxyfumagillol derivative represented by Chemical Formula 1.

The present invention relates to a 5-demethoxyfumagillol derivative represented by Chemical Formula 1 or a pharmaceutically acceptable salt thereof:

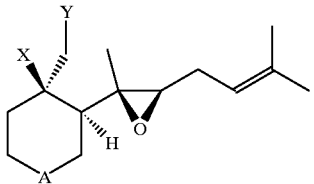

1 wherein, X is hydroxy, Y is a halogen or

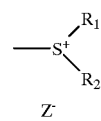

($R_1$ and $R_2$ individually represent hydrogen, or substituted or unsubstituted lower alkyl, and $Z^-$ represents a counter ion, provided that $R_1$ and $R_2$ do not represent hydrogen at the same time), or X and Y may be connected to form an oxirane ring, and

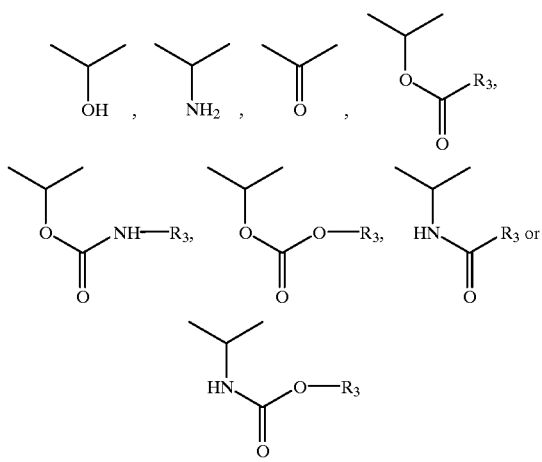

($R_3$ is substituted or unsubstituted lower alkyl or alkanoyl; substituted or unsubstituted aryl or arylalkyl; or arylalkanoyl).

Among the compounds of Chemical Formula 1, prefered are those compounds or pharmaceutically acceptable salts thereof, wherein, X is hydroxy, Y is a halogen or

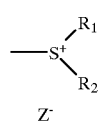

($R_1$ and $R_2$ individually represent hydrogen, or lower alkyl, and $Z^-$ represents a counter ion, provided that $R_1$ and $R_2$ do not represent hydrogen at the same time), or X and Y may be connected to form an oxirane ring, and —A— represents

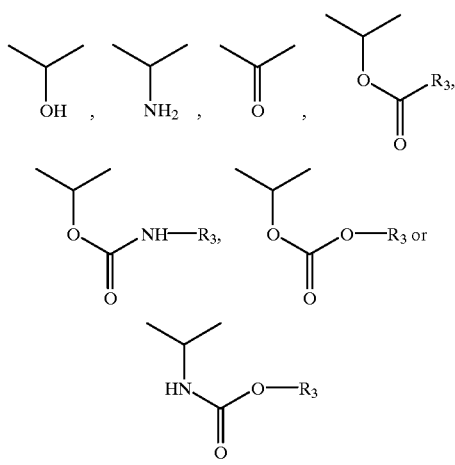

($R_3$ is substituted or unsubstituted lower alkyl or alkanoyl; substituted or unsubstituted aryl or arylalkyl).

Among the compounds of Chemical Formula 1, more preferred are
5-demethoxy-6-oxo-6-deoxyfumagillol;
5-demethoxyfumagillol;
3-chloromethyl-5-demethoxy-3-hydroxy-6-oxo-6-deoxyfumagillol;
5-demethoxy-6-O-cinnamoylfumagillol;
5-demethoxy-6-O-(3,4,5-trimethoxy)cinnamoyl fumagillol;
5-demethoxy-6-O-(4-chlorocinnamoyl)fumagillol;
4-O-chloroacetylcarbamoyl- 1-chloromethyl-1-cyclohexanol;
5-demethoxy-6-O-[3-(4-methoxyphenyl)propionyl] fumagillol;
O-benzyloxycarbonyl-5-demethoxyfumagillol;
6-amino-5-demethoxy-6-deoxyfumagillol;
6-(4-methoxycinnamoyl)amino-5-demethoxy-6-deoxyfumagillol;
6-(4-dimethylaminocinnamoyl)amino-5-demethoxy-6-deoxyfumagillol;
6-[3-(4-methoxyphenyl)propionyl]amino-6-deoxy-5-demethoxyfumagillol;
2-(1,2-epoxy- 1,5-dimethyl-4-hexenyl)-1-methylthiomethyl-1,4-cyclohexanediol;
4-O-(chloroacetylcarbamoyl)-2-(1,2-epoxy-1,5-dimethyl-4-hexenyl) -1-methylthiomethyl-1-cyclohexanol;
4-O-(chloroacetylcarbamoyl)-2-(1,2-epoxy- 1,5-dimethyl-4- hexenyl)-1-dimethylsulfoniomethyl-1-cyclohexanol iodide;
2-(1,2-epoxy-1,5-dimethyl-4-hexenyl)-1-methylthiomethyl-4-oxo-1-cyclohexanol; and
2-(1,2-epoxy-1,5-dimethyl-4-hexenyl)-1-dimethylsulfoniomethyl4-oxo-1-cyclohexanol iodide.

The compounds of Chemical Formula 1 can be prepared by various processes, but typically via carbamoylation, acylation and carbonation. These processes are explained by means of Reaction Schemes here-in-below:

(1) Acylation

Scheme 1.

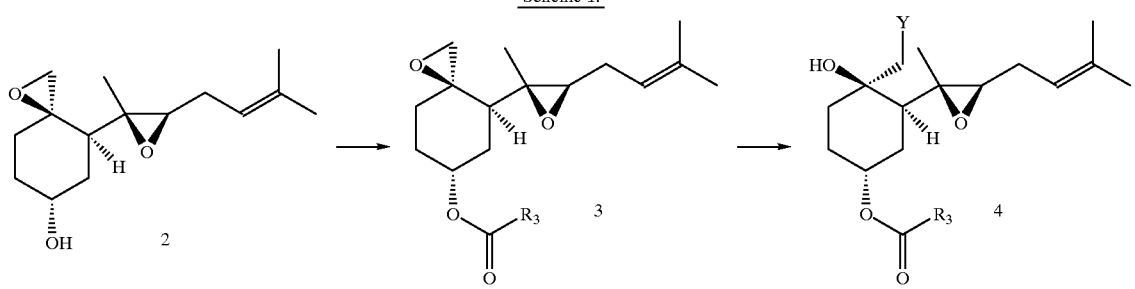

-continued

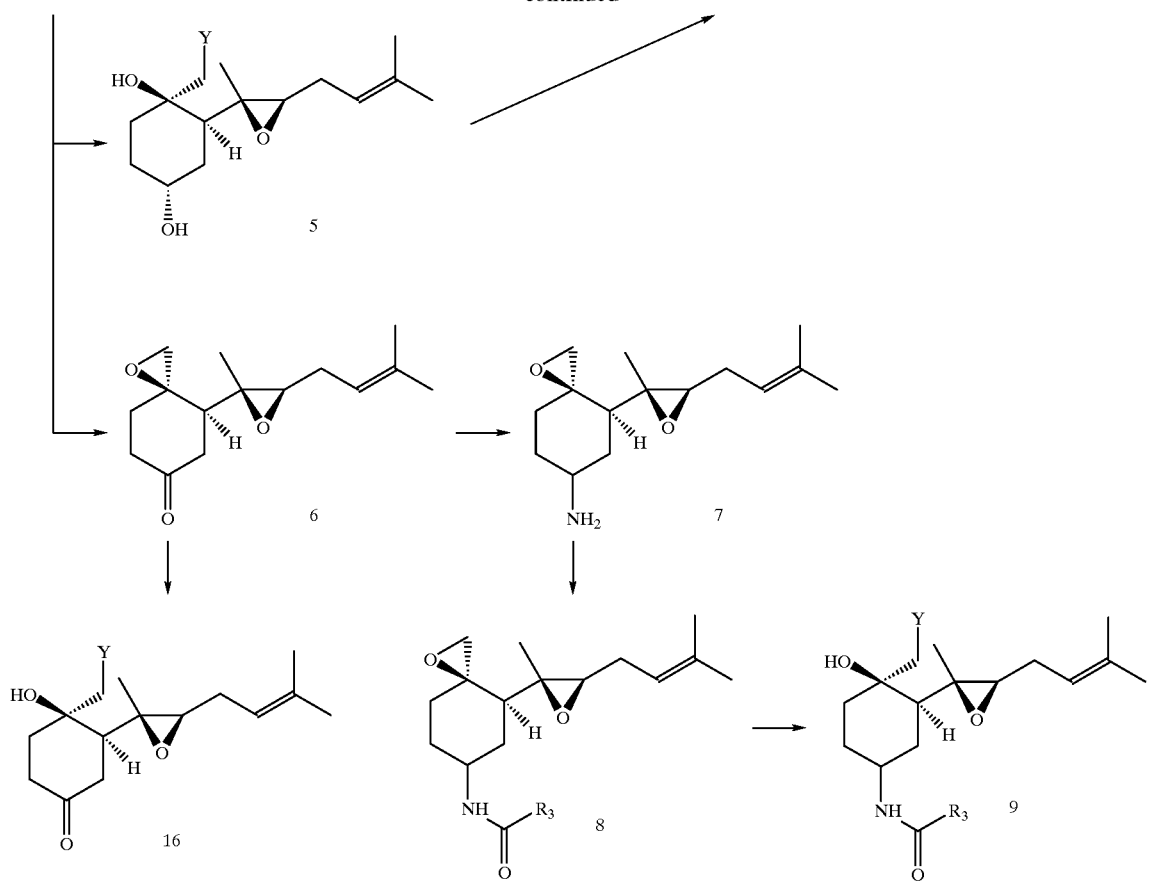

In the Formula, $R_3$ and Y are the same as defined in the above.

The acylation of Reaction Scheme 1 is performed by reacting a compound of Chemical Formula 2 as a starting material with a carboxylic acid derivative having high reactivity in the presence of a base to obtain a compound represented by Chemical Formula 3, which is then subjected to oxirane ring opening reaction to obtain a compound represented by Chemical Formula 4. Alternatively, a compound of Chemical Formula 2 is firstly subjected to oxirane opening reaction to provide a compound represented by Chemical Formula 5, which is then reacted with a carboxylic acid derivative having high reactivity to obtain a compound of Chemical Formula 4.

Otherwise, a compound of Chemical Formula 2 is subjected to an oxidation using pyridine and chromium oxide ($CrO_3$) to provide a compound of Chemical Formula 6, which is then subjected to reductive amination using ammonium acetate and sodium cyanoborohydride to obtain a compound of Chemical Formula 7. The compound of Chemical Formula 7 is reacted with a carboxylic acid derivative having high reactivity to give a compound of Chemical Formula 8, which is then subjected to oxirane ring opening reaction to obtain a compound of Chemical Formula 9.

The hydroxy group of a compound of Chemical Formula 2 can be oxidized to give a compound of Chemical Formula 6, which is then subjected to oxirane ring opening reaction to obtain a compound of Chemical Formula 16.

The carboxylic acid derivatives which can be used in the acylation include acid anhydrides, mixed anhydrides, acid chloride, acid p-toluensulfonic anhydrides and acid mesylic anhydrides. The carboxylic acid derivative can be used in an amount of 1 to 10 equivalents, preferably 1 to 3 equivalents on the basis of the amount of the compound of Chemical Formula 2.

As a base used in the acylation, a tertiary amine such as triethyl amine, diisopropylethyl amine, pyridine and dimethylaminopyridine, or an alkaline metal hydride such as sodium hydride and potassium hydride may be used in an amount of 1 to 10 equivalents, preferably, 1 to 3 equivalents.

As a solvent for the acylation, dimethylformamide, dichloromethane, chloroform, diethyl ether, tetrahydrofuran, dioxane, acetonitrile, benzene or toluene may be used. Among the solvents, preferred are dimethylformamide, dichloromethane, tetrahydrofuran, acetonitrile and benzene.

The reaction temperature of acylation is −80 to 100° C., preferably 0 to 50° C.

The oxirane ring opening reaction can be performed by reacting the reactant with an amount of 1 to 3 equivalent of acid, with a salt in the presence of an acid catalyst, or with a thiol in the presence of a base.

As an acid used for the oxirane ring opening reaction in an amount of 1 to 3 equivalents, hydrochloric acid, bromic acid or iodic acid is preferably used.

As a catalyst for the oxirane ring opening reaction, acetic acid, sulfuric acid, p-toluenesulfonic acid, hydrochloric acid, phosphoric acid or nitric acid may be used, but preferred is acetic acid or hydrochloric acid.

As a salt used for the oxirane ring opening reaction, lithium bromide, lithium chloride, sodium chloride, potassium chloride, potassium bromide, sodium bromide, potassium iodide, sodium iodide or lithium iodide may be used. Among these salts, lithium chloride, lithium bromide and lithium iodide are preferred.

As a solvent for the oxirane ring opening reaction, tetrahydrofuran, acetonitrile, dichloromethane, methanol or ethanol may be used, and the reaction temperature is −80 to 100° C., preferably 0 to 50° C.

(2) Carbamoylation same process employed in (1) acylation to obtain a compound of Chemical Formula 11. Alternatively, oxirane ring opening reaction is firstly performed to give a compound of Chemical Formula 5, which is then carbamoylated to obtain a compound of Chemical Formula 11.

Otherwise, a compound of Chemical Formula 2 is subjected to oxidation using pyridine and chromium oxide ($CrO_3$) to give a compound of Chemical Formula 6, which

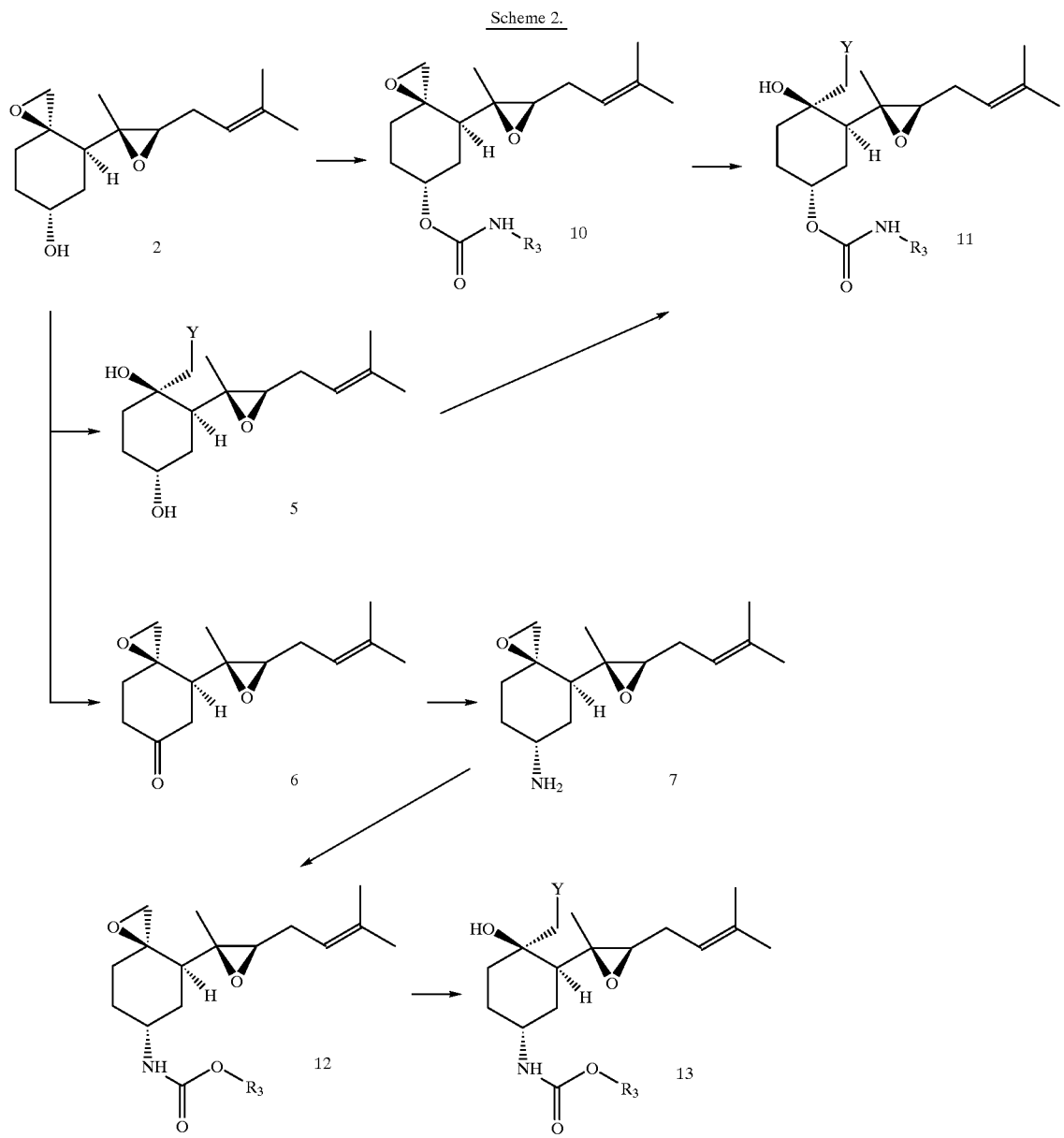

In the Formula, $R_3$ and Y are the same as defined in the above.

In the carbamoylation shown in Reaction Scheme 2, a compound of Chemical Formula 2 as a starting material is reacted with phenyl chloroformate or 4-nitrophenylchloroformate in the presence of sodium hydride or dimethylaminopyridine, and then reacted with amine in the presence or absence of a base to give a compound of Chemical Formula 10, which is further subjected to oxirane ring opening reaction according to the is subjected to reductive amination using ammonium acetate and sodium cyanoborohydride to provide a compound of Chemical Formula 7, which is further subjected to carbamoylation as above to obtain a compound of Chemical Formula 12, which is then subjected to oxirane ring opening to obtain a compound of Chemical Formula 13.

According to the carbamoylation, a compound of Chemical Formula 2 or 5 can be reacted with an isocyanate represented by $R_3NCO$ in the presence of a base to obtain a compound of Chemical Formula 10 or 11.

As a base used in the carbamoylation, a tertiary amine such as triethyl amine, diisopropylethyl amine, pyridine and dimethylaminopyridine, or sodium hydride may be used in an amount of 1 to 10 equivalents, preferably, 1 to 3 equivalents.

As a solvent for the carbamoylation, methanol, ethanol, tetrahydrofuran, dimethylformamide, acetonitrile, dioxane, dichloromethane or chloroform may be used. Among the solvents, preferred are methanol, ethanol, dichloromethane and dioxane.

The reaction temperature of the carbamoylation is −20 to 100° C., preferably 0 to 50° C.

(3) Carbonation

15. Alternatively, a compound of Chemical Formula 2 is firstly subjected to oxirane opening reaction to provide a compound represented by Chemical Formula 5, which is then subjected to the carbonation described above to obtain a compound of Chemical Formula 15.

As a base used in the carbonation, sodium hydride or dimethylaminopyridine may be used in an amount of 1 to 10 equivalents, preferably, 1 to 3 equivalents to the compound of Chemical Formula 2.

As a solvent for the carbonation, tetrahydrofuran, dichloromethane, chloroform, dioxane, dimethylformamide, benzene or toluene may be used. Among the solvents, preferred are tetrahydrofuran, dichloromethane, chloroform and dimethylformamide.

Scheme 3.

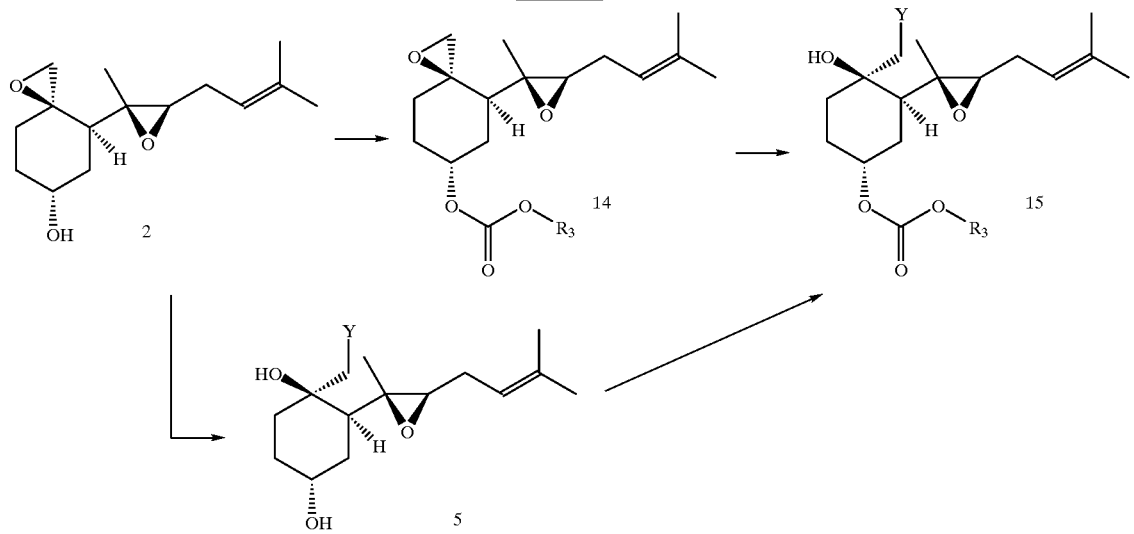

In the Formula, $R_3$ and Y are the same as defined in the above.

In the carbonation shown in Reaction Scheme 3, a compound of Chemical Formula 2 as a starting material is reacted with a chloroformate in the presence of a base to provide a compound represented by Chemical Formula 14, which is then subjected to oxirane ring opening reaction according to the same procedure employed in (1) acylation described above to obtain a compound of Chemical Formula The reaction temperature of the carbonation is −10 to 100° C., preferably 20 to 80° C.

The compound of Chemical Formula 2, a starting material commonly used in (1) acylation, (2) carbamoylation and (3) carbonation, is a novel compound, which can be prepared via a process shown in Reaction Scheme 4 starting from a known compound.

Scheme 4.

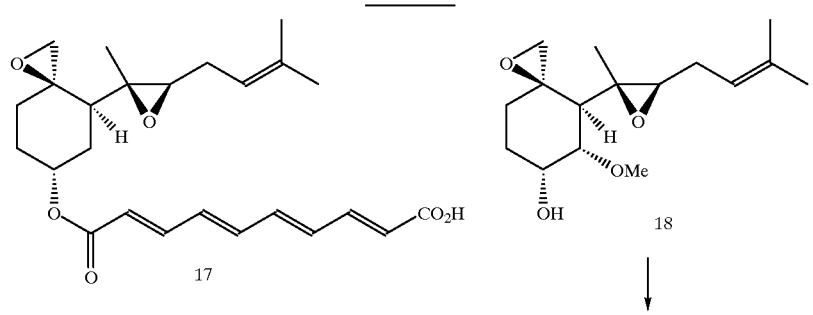

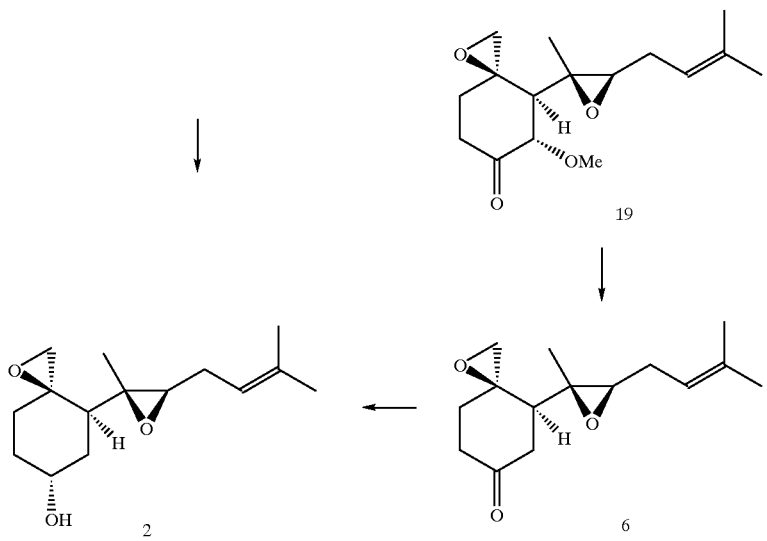

Metabolic product of *Aspergillus fumigatus* (IMI-069714) is isolated and purified to obtain 5-demethoxyfumagillin of Chemical Formula 17, which is then reacted with a base to give the compound of Chemical Formula 2. Alternatively, fumagillol [Tarbell, D. S. et al., *J Am. Chem. Soc.*, 83, 3096 (1961)] represented by Chemical Formula 18, which is a hydrolyte of fumagillin, is subjected to oxidation to give a carbonyl compound of Chemical Formula 19, which is then reacted with samarium iodide ($SmI_2$) [Molander, G. A., Hahn, G., *J. Org. Chem.*, 51, 1135 (1986)] to provide a novel demethoxy compound of Chemical Formula 6, which is then reduced to obtain the compound of Chemical Formula 2.

The present invention also provides an angiogenesis inhibiting composition which comprises a therapeutically effective amount of the compound of Chemical Formula 1 or a salt thereof as an active ingredient, and a pharmaceutically acceptable carrier.

A compound of Chemical Formula 1 and a salt thereof according to the present invention may be formulated as a pharmaceutical solid, semisolid or liquid type formulation which is suitable for oral or parenteral administration by blending the compound or salt with a pharmaceutically acceptable inert carrier.

As the compounds of Chemical Formula 1 or salts have excellent angiogenesis inhibiting effect, they can be used as an anticancer medicine or an inhibitor for a cancer transfer, or a therapeutic agent for treating rheumatic arthritis, psoriasis or diabetic retinitis.

In order to evaluate general toxicity of the compound of Chemical Formula 1 according to the present invention, experiments on acute toxicity were carried out by using mice. As a result, the half lethal dose ($LD_{50}$) of each compound in case of oral administration was not less than 2.5 g/kg, thereby the compound was evaluated as a considerably safe compound.

Thus, the compound of Chemical Formula 1 according to the present invention may be administered in an amount of 0.1 mg/kg to 2.5 g/kg per day, more preferably 0.2 to 200 mg/kg for the first stage. But the dose may be varied depending on the requirement of a patient, the condition of disease to be treated, and the compound to be used.

The invention is described in more detail by referring to the examples below, but it should be noticed that the present invention is not restricted to the examples by any means.

EXAMPLE 1

Culture and Purification of 5-demethoxyfumagillin

A suspension of spores [$5.8 \times 10^8$ spores/ml, 10% glycerol, 1% Tween 80, 5% lactose (w/v)] of *Aspergillus fumigatus* (IMI-069714) was inoculated in CGC pre-culture medium (CSL 40 g/L, glucose 30 g/L, $CaCO_3$ 10 g/L) in a concentration of 1% (v/v), and cultured with rotary shaking at 28° C. for 30 hours. The resultant pre-culture medium was inoculated in 18 L of CGC culture medium (CSL 50 g/L, glucose 30 g/L, $CaCO_3$ 10 g/L) in a concentration of 1%, and cultured in a 30 L jar fermentor at 25° C. for 60–70 hours.

The cultured medium was filtered through a filter paper, and the filtrate (about 12 L) was passed through an HP-20 column (about 1L) to adsorb the active material. The adsorbed HP-20 column was washed with 5 L of 50% aqueous methanol, and eluted with 5 L of methanol/ethanol (1/1) solution. The active portions are combined and concentrated under reduced pressure. A proper amount of chloroform was added to the residue to dissolve the active material. To the chloroform solution, the same amount of distilled water was added, and the mixture was stirred for 10 to 20 minutes. The mixture was centrifuged to separate chloroform layer, and the layer was concentrated under reduced pressure. About 15 g of the concentrate was adsorbed on a silica gel column of 400 ml volume, and eluted with a mixed solvent of chloroform/methanol (10:0.5). The active portions were combined and concentrated under reduced pressure (about 500 mg), and dissolved in a small amount of ethyl acetate. The solution was stood overnight at −20° C. to induce precipitation. The precipitated fumagillin mixed material (200 mg) was washed with cold ethyl acetate twice or three times to obtain a mixed sample having high purity. The sample was separated by medium performance liquid chromatography (MPLC) using a solvent system of dichloromethane/methanol (100:1) to obtain 11 mg of 5-demethoxyfumagillin.

$^1$H NMR ($CDCl_3$) δ:7.33~7.21 (m, 2H), 6.64~6.59 (m, 2H), 6.51~6.46 (m, 2H), 5.95 (dd, 2H, J=4.04, 15.3 Hz), 5.36 (brs, 1H), 5.19 (t, 1H, J=7.54 Hz), 2.91 (d, 1H, J=4.36 Hz), 2.71 (t, 1H, J=6.4 Hz), 2.56 (d, 1H, J=4.36 Hz), 2.45~2.35 (m, 1H), 2.17~1.79 (m, 7H), 1.75 (s, 3H), 1.66 (s, 3H), 1.15 (s, 3H), 0.93~0.88 (m, 1H)

$^{13}$C NMR (CDCl$_3$) δ: 167.02, 166.38, 144.23, 143.89, 139.48, 139.29, 135.39, 134.06, 133.89, 125.29, 123.55, 118.75, 69.38, 64.45, 60.57, 59.59, 51.52, 43.61, 30.55, 30.23, 28.13, 27.95, 18.38, 18.15, 14.13

EXAMPLE 2

5-Demethoxyfumagillol (Hydrolysis of 5-demethoxyfumagillin)

To 5-demethoxyfumagillin (120 mg), 0.1 N sodium hydroxide solution (12 ml) was added, and the mixture was stirred at room temperature for 6 hours. The reaction mixture was diluted with ethyl ether (50 ml), and the organic layer was washed with water (10 ml) and brine (10 ml), and dried over anhydrous magnesium sulfate. After filtering, the solvent was removed from the filtrate by evaporating under reduced pressure. The residue was purified by silica gel column chromatography (eluent: ethyl acetate/n-hexane= 1:1) to obtain 51 mg of colorless oil.

$^1$H NMR (CDCl$_3$) δ: 5.19~5.15 (m, 1H), 4.31~4.29 (m, 1H), 2.86 (d, 1H, J=4.4 Hz), 2.70 (dd, 1H, J=7.1, 5.9 Hz), 2.52 (d, 1H, J=4.4 Hz), 2.39 (m, 1H), 2.42~2.33 (m, 1H), 2.27~1.78 (m, 7H), 1.74 (s, 3H), 1.65 (s, 3H), 1.14 (s, 3H), 1.12~1.03 (m, 1H)

$^{13}$C NMR (CDCl$_3$) δ: 135.28, 118.76, 6.01, 64.59, 60.82, 60.05, 51.49, 42.54, 33.54, 30.60, 29.57, 27.99, 26.12, 18.38, 14.06

EXAMPLE 3

5-Demethoxyfumagillol (Process using samarium iodide)

Fumagillol was oxidized by a conventional process [Marui, S., Kishimoto, S., *Chem. Pharm. Bull.*, 40, 575 (1992)] to obtain a ketone compound (19). To the ketone compound(19) (300 mg), tetrahydrofuran (6 ml) and methanol (1 ml) were added dropwise, and the mixture was chilled to −78° C., and then, samarium iodide (0.1 M SmI$_2$ solution, 21 ml) was slowly added dropwise thereto. After stirring for 30 minutes, the reaction temperature was raised to room temperature, and the mixture was further stirred for 30 minutes. To the reaction mixture, saturated potassium carbonation solution (300 ml) was added, and the mixture was extracted with ethyl acetate (100 ml). The organic layer was washed with water (20 ml) and brine (20 ml), dried over anhydrous magnesium sulfate and filtered. After removing the reaction solvent by evaporation under reduced pressure, the residue was purified by silica gel column chromatography (eluent: ethyl acetate / n-hexane =1/2) to obtain 200 mg of the ketone compound (6) as a colorless oil.

$^1$H NMR (CDCl$_3$) δ: 5.16 (t, 1H, J=10.18 Hz), 2.94 (d, 1H, J=4.46 Hz), 2.76~2.54 (m, 6H), 2.44~2.37 (m, 2H), 2.16~1.81 (m, 5H), 1.75 (s, 3H), 1.66 (s, 3H), 1.26 (s, 3H)

The ketone compound (6) was dissolved in methanol (10 ml), and sodium borohydride (20 mg) was added thereto. After stirring the mixture 30 minutes, methanol was distilled off therefrom under reduced pressure, and the residue was diluted with ethyl acetate (50 ml). The organic layer was washed with water (10 ml), dried over anhydrous magnesium sulfate and filtered. The residue after removing the solvent by evaporation under reduced pressure was purified by silica gel column chromatography (ethyl acetate/n-hexane=1/1) to obtain 80 mg of colorless oil. The analytical results were identical to those of the compound obtained in Example 2.

EXAMPLE 4

3-Chloromethyl-5-demethoxy-3-hydroxy-6-oxo-6-deoxyfumagillol

To a solution of 5-demethoxyketone (6) (300 mg) of Example 3 in tetrahydrofuran, acetic acid (0.2 ml) and lithium chloride (100 mg) were added at room temperature, and the mixture was stirred for 36 hours. After removing the solvent by evaporation under reduced pressure, the residue was purified by silica gel column chromatography (eluent: ethyl acetate/n-hexane=1/1) to obtain 350 mg of white solid.

$^1$H NMR (CDCl$_3$) δ: 5.17~5.13 (m, 1H), 3.72 (q, 2H, J=11.2 Hz), 2.87~2.68 (m, 4H), 2.43~2.06 (m, 5H), 1.92~1.85 (m, 2H), 1.75 (s, 3H), 1.66 (s, 3H), 1.41 (s, 3H)

EXAMPLE 5

5-Demethoxy-6-O-chloroacetylcarbamoylfumagillol

To a solution of 5-demethoxyfumagillol (100 mg) in dichloromethane (2 ml) cooled to 0° C., dimethylaminopyridine (28 mg) and chloroacetyl isocyanate (0.068 ml) were added, and the mixture was stirred for 1 hour. After removing the solvent by evaporation under reduced pressure, the residue was purified by silica gel column chromatography (eluent: ethyl acetate / n-hexane =1/4) to obtain 102 mg of white solid.

$^1$HNMR(CDCl$_3$) δ: 7.83 (brs,1H), 5.16 (t, 1H, J=7.3 Hz), 4.83 (m,1H), 4.49 (s, 2H), 2.92 (d, 1H, J=4.2 Hz), 2.66 (m, 1H), 2.60 (d, 1H, J=4.2 Hz), 2.41~1.81 (m, 8H), 1.75 (s, 3H), 1.65 (s, 3H), 1.16 (s, 3H), 1.30 (m, 1H)

EXAMPLE 6

5-Demethoxy-6-O-cinnamoylfumagillol

① To a solution of 5-demethoxyfumagillol (110 mg) in tetrahydrofuran (3 ml), 60% sodium hydride (26 mg) was added at room temperature, and the mixture was stirred for an hour.

② To a solution of cinnamic acid (112 mg) in dichloromethane (3ml), methanesulfonyl chloride (0.05 ml) and triethylamine (0.1 ml) were added. After stirring for 1 hour, the mixture was added to the solution of ①, and the resultant mixture was stirred for 1 hour. To the reaction mixture, water (5 ml) and ethyl acetate (50 ml) were added. The organic layer was separated, and washed with brine (5 ml), dried over anhydrous magnesium sulfate, and filtered. After removing the solvent by evaporation under reduced pressure, the residue was purified by silica gel column chromatography (eluent: ethyl acetate/n-hexane=1/3) to give the title compound (82 mg) as powder.

$^1$H NMR (CDCl$_3$) δ: 7.57 (d, 1H, J=15.9 Hz), 7.54~7.38 (m, 5H), 6.34 (d, 2H, J=15.9 Hz), 5.41 (brs, 1H), 5.19 (brt, 1H, J=7.6 Hz), 2.93 (d, 1H, J=4.3 Hz), 2.75 (t, 1H, J=6.4 Hz), 2.57 (d,1H, J=4.3 Hz), 2.45~1.82 (m, 8H), 1.74 (s, 3H), 1.65 (s, 3H), 1.14 (s, 3H), 1.12~1.03 (m, 1H)

EXAMPLE 7

5-Demethoxy-6-O-(3,4,5-trimethoxy)cinnamoyl fumagillol

The same procedure as Example 6 was repeated but using fumagillol (95 mg), 60% sodium hydride (21 mg), 3,4,5-trimethoxycinnamic acid (95 mg), triethylamine (0.095 ml) and methanesulfonyl chloride (43 μl), to give 68 mg of the title compound as white solid.

$^1$H NMR (CDCl$_3$) δ: 7.57 (d,1H, J=15.9 Hz), 6.76 (s, 2H), 6.34 (d,1H, J=15.9 Hz), 5.40 (brs, 1H), 5.19 (m, 1H), 3.89 (3s, 9H), 2.93 (d, 1H, J=4.3 Hz), 2.75 (t, 1H, J=6.4 Hz), 2.57 (d, 1H, J=4.3 Hz), 2.45~1.82 (m, 8H), 1.74 (s, 3H), 1.65 (s, 3H), 1.14 (s, 3H), 1.11~1.03 (m, 1H)

EXAMPLE 8

5-Demethoxy-6-O-(4-chlorocinnamoyl)fumagillol

The same procedure as Example 6 was repeated but using 5-demethoxyfumagillol (95 mg), 60% sodium hydride (21 mg), 4-chlorocinnamic acid (71 mg), triethylamine (0.94 ml) and methane sulfonyl chloride (41 μl), to give 52 mg of the title compound as white solid.

$^1$H NMR (CDCl$_3$) δ: 7.62 (d, 1H, J=15.9 Hz), 7.45 (d, 2H, J=8.5 Hz), 7.36 (d, 2H, J=8.5 Hz), 6.46 (d, 1H, J=15.9 Hz), 5.22 (t, 1H, J=7.7 Hz), 3.01 (d,1H, J=4.3 Hz), 2.62 (t, 1H, J=6.3 Hz), 2.57 (d, 1H, J=4.3 Hz), 2.38~1.81 (m, 8H), 1.75 (s, 3H), 1.67 (s, 3H), 1.24 (s, 3H)

EXAMPLE 9

4-O-chloroacetylcarbamoyl-l-chloromethyl-l-cyclohexanol

To a solution of the compound (100 mg) of Example 5 in tetrahydrofuran (2 ml), lithium chloride (8 mg) and acetic acid (0.1 ml) were added, and the mixture was stirred at 30° C. for 36 hours. After adding water (10 ml) and ethyl acetate (50 ml) to the reaction mixture, the organic layer was separated, washed with brine (10 ml), dried over anhydrous magnesium sulfate, and filtered. The solvent was evaporated under reduced pressure, and the residue was purified by silica gel column chromatography (eluent: ethyl acetate/n-hexane=1/2) to obtain the title compound (105 mg) as white solid.

$^1$H NMR (CDCl$_3$) δ: 7.82 (brs, 1H), 5.47 (brs,1H), 5.16 (t, 1H, J=7.3 Hz), 4.49 (s, 2H), 3.76 (d, 1H, J=10.9 Hz), 3.51 (d, 1H, J=10.9 Hz), 3.3~3.21 (m, 1H), 2.97 (m,1H), 2.47~1.25 (m, 8H), 1.74 (s, 3H), 1.66 (s, 3H), 1.32 (s, 3H)

EXAMPLE 10

5-Demethoxy-6-O-[3-(4-methoxyphenyl)propionyl] fumagillol

To a solution of 5-demethoxyfumagillol (100 mg) in tetrahydrofuran (3 ml), 60% sodium hydride (20 mg) was added at room temperature, and the mixture was stirred for 1 hour. To the reaction mixture, 3-(4-methoxyphenyl) propionyl chloride (0.12 ml) was added at room temperature, and the mixture was stirred for 8 hours. Water (5 ml) and ethyl acetate (50 ml) were added thereto, and the organic layer was separated, washed with brine (5 ml), dried over anhydrous magnesium sulfate and filtered. The residue after evaporating the solvent under reduced pressure was purified by column chromatography (eluent: ethyl acetate/n-hexane=1/2) to obtain 72 mg of the title compound as white powder.

$^1$H NMR (CDCl$_3$) δ: 7.47 (d, 2H, J=8.7 Hz), 6.90 (d, 2H, J=8.7 Hz), 5.74 (m, 1H), 5.23 (t,1H, J=7.4 Hz), 3.84 (s, 3H), 3.01 (d,1H, J=4.3 Hz), 2.72 (t, 1H, J=6.5 Hz), 2.57 (d, 1H, J=4.3 Hz), 2.39~1.8 (m, 12H), 1.75 (s, H), 1.67 (s, 3H), 1.24 (s, 3H), 1.12 (m, 1H)

EXAMPLE 11

O-benzyloxycarbonyl-5-demethoxyfumagillol

The same procedure as Example 10 was repeated but using 5-demthoxyfumagillol (100 mg), 60% sodium hydride (20 mg) and carobenzyloxy chloride (0.074 ml), to give 84 mg of the title compound as white solid.

$^1$H NMR (CDCl$_3$) δ: 7.41~7.26 (m, 5H), 5.49 (brs, 1H), 5.21 (m, 1H), 5.19 (d,1H, J=12.1 Hz), 5.09 (d, 1H, J=12.1 Hz), 2.97 (d, 1H, J=4.3 Hz), 2.66 (m,1H), 2.53 (s,1H, J=4.3 Hz), 2.35~1.79 (m, 8H), 1.74 (s, 3H), 1.65 (s, 3H), 1.25 (s, 3H), 0.87 (m, 1H)

EXAMPLE 12

6-Amino-5-demethoxy-6-deoxyfumagillol

To a solution of 5-demethoxyketone (6) (500 mg) of Example 3 in methanol (15 ml), ammonium acetate (1.4 g) and sodium cyanoborohydride (110 mg) were added. After stirring the mixture at room temperature for 1 hour, the solvent was distilled off under reduced pressure, and the residue was diluted with ethyl acetate (100 ml). The organic layer was wshed with saturated sodium hydrogen carbonate (20 ml), dried over anhydrous magnesium sulfate, filtered. After removing the solvent by evaporation under reduced pressure, 150 mg of colorless oil was obtained.

$^1$H NMR (CDCl$_3$) δ: 5.21 (m, 5H), 3.66 (m, 1H), 2.89 (s, 1H, J=4.2 Hz), 2.58 (t,1H, J=7.1 Hz), 2.51 (d,1H, J=4.2 Hz), 2.41~1.79 (m, 8H), 1.75 (s, 3H), 1.65 (s, 3H), 1.16 (s, 3H), 0.98 (m, 1H)

EXAMPLE 13

6-(4-Methoxycinnamoyl)amino-5-demethoxy-6-deoxyfumagillol

To a solution of the compound (200 mg) obtained from Example 12 in dichloromethane (4 ml), pyridine (0.2 ml) and cinnamic methane sulfonate (278 mg) obtained according to the same procedure as Example 6 were added, and the mixture was stirred for 2 hours. The reaction mixture was diluted with ethyl acetate (100 ml), and the organic layer was washed with saturated sodium hydrogen carbonate solution (10 ml), dried over anhydrous magnesium sulfate, and filtered. The residue after distilling off the solvent under reduced pressure was purified by silica gel column chromatography (eluent: ethyl acetate/n-hexane=1/4) to obtain 160 mg of white solid.

$^1$H NMR (CDCl$_3$) δ: 7.63 (d, 1H, J=15.9 Hz), 7.47 (d, 2H, J=8.7 Hz), 6.90 (d, 2H, J=8.7Hz), 6.36 (d, 2H, J=15.9Hz), 5.97 (m,1H), 5.20 (m, 1H), 3.84 (s, 3H), 3.01 (s,1H, J=4.2 Hz), 2.58 (t,1H, J=7.1 Hz), 2.51 (d, 1H, J=4.2 Hz), 2.41~1.79 (m, 8H), 1.75 (s, 3H), 1.65 (s, 3H), 1.16 (s, 33H), 0.98 (m, 1H)

EXAMPLE 14

6-(4-Dimethylaminocinnamoyl)amino-5-demethoxy-6-deoxyfumagillol

The same procedure as Example 13 was carried out using the compound (100 mg) of Example 12, pyridine (0.1 ml), 4-dimethylaminocinnamic acid (70 mg) and methanesulfonyl chloride (43 μl), to obtain 68 mg of the title compound as white solid.

$^1$H NMR (CDCl$_3$) δ: 7.4 (d,1H, J=15.6 Hz), 7.32 (m, 2H), 6.65 (d, 1H, J=15.6 Hz), 6.5 (m, 2H), 5.96 (m,1H), 5.21 (m, 1H), 3.04 (s, 6H), 3.01 (d, 1H, J=4.3 Hz), 2.58 (t, 1H, J=7.1 Hz), 2.51 (d, 1H, J=4.3 Hz), 2.41~1.79 (m, 8H), 1.75 (s, 3H), 1.65 (s, 3H), 1.16 (s, 3H), 0.98 (m, 1H)

EXAMPLE 15

6-[3-(4-Methoxyphenyl)propionyl]amino-6-deoxy-5-demethoxyfumagillol

To a solution of the compound (100 mg) obtained from Example 12 in dichloromethane (3 ml), pyridine (0.1 ml) and 3-(4-methoxyphenyl)propionyl chloride (0.12 ml) were added, and the mixture was stirred at room temperature for 3 hours. The reaction mixture was diluted with ethyl acetate (100 ml), and the organic layer was washed with water (20 ml) and brine (20 ml), dried over anhydrous magnesium sulfate, and filtered. The residue after distilling off the solvent under reduced pressure was purified by silica gel column chromatography (eluent: ethyl acetate/n-hexane=1/4) to obtain 82 mg of the title compound as solid.

$^1$H NMR (CDCl$_3$) δ: 7.47 (d, 2H, J=8.7 Hz), 6.90 (d, 2H, J=8.7 Hz), 5.96 (m, 1H), 5.21 (m,1H), 3.01 (d, 1H, J=4.3 Hz), 2.58 (t, 1H, J=7.1 Hz), 2.51 (d, 1H, J=4.3 Hz), 2.41~1.79 (m, 12H), 1.75 (s, 3H), 1.65 (s, 33H), 1.16 (s, 3H), 0.98 (m, 1H)

EXAMPLE 16

2-(1,2-Epoxy-1,5-dimethyl-4-hexenyl)-1-methylthiomethyl-1,4-cyclohexanediol

To a solution of 5-demethoxyfumagillol (280 mg) in N,N'-dimethylformamide (2 ml), thiomethoxide (220 mg) was added, and the mixture was stirred at room temperature for 1 hour. After adding water (20 ml) thereto, the reaction mixture was extracted with isopropyl ether (50 ml). The organic layer was washed with saturated sodium hydrogen carbonate solution (10 ml) and brine (20 ml), dried over anhydrous magnesium sulfate, and filtered. The residue after distilling off the solvent under reduced pressure was purified by silica gel column chromatography (eluent: ethyl acetate/n-hexane=1/2) to obtain 180 mg of the title compound as white solid.

$^1$H NMR (CDCl$_3$) δ: 5.16 (m, 1H), 4.21 (m, 1H), 3.48~2.92 (m, 3H), 2.51~1.65 (m, 8H), 2.08 (s, 3H) 1.74 (s, 3H), 1.66 (s, 3H), 1.45 (s, 3H), 0.98 (m, 1H)

EXAMPLE 17

4-O-(chloroacetylcarbamoyl)-2-(1,2-epoxy-1,5-dimethyl-4-hexenyl)-1-methylthiomethyl-1-cyclohexanol A solution of the compound of (140 mg) Example 16 in dichloromethane (2 ml) was chilled to 0° C., and dimethylaminopyridine (110 mg) and chloroacetyl isocyanate (0.04 ml) were added thereto. After stirring the mixture for 30 minutes, ethyl acetate was added thereto, and the organic layer was washed with saturated sodium hydrogen carbonate solution (10 ml) and brine (10 ml), dried over anhydrous magnesium sulfate, and filtered. The residue after distilling off the solvent under reduced pressure was purified by silica gel column chromatography (eluent: ethyl acetate/n-hexane=1/4) to obtain 130 mg of the title compound as white solid.

$^1$H NMR (CDCl$_3$) δ: 7.68 (brs, 1H), 5.46 (m, 1H), 5.16 (m, 1H), 4.51 (s, 2H), 3.48 (m, 2H) 2.42~1.62 (m, 8H),, 2.08 (s, 3H), 1.74 (s, 3H), 1.66 (s, 3H), 1.44 (s 3H), 0.98 (m, 1H)

EXAMPLE 18

4-O-(chloroacetylcarbamoyl)-2-(1,2-epoxy-1,5-dimethyl-4-hexenyl)-1-dimethylsulfoniomethyl-1-cyclohexanol iodide To a solution of the compound (120 mg) of Example 17 in acetonitrile (2 ml), methyl iodide (0.18 ml) was added dropwise, and the mixture was stirred at room temperature for 8 hours. The solvent was removed by evaporation under reduced pressure, and ether (3 ml) was added to the residue. The solid precipitated was filtered to obtain white solid (130 mg)

$^1$H NMR (CDCl$_3$) δ: 7.68 (brs, 1H), 5.46 (m,1H), 5.16 (m, 1H), 4.51 (s, 2H), 3.48 (m, 2H), 2.42~1.62 (m, 8H), 2.09 (s, 6H), 1.74 (s, 3H), 1.66 (s, 3H), 1.44 (s, 3H), 0.98 (m, 1H)

EXAMPLE 19

2-(1,2-Epoxy-1,5-dimethyl-4-hexenyl)-1-methylthiomethyl-4-oxo-1 -cyclohexanol

The same procedure as Example 16 was repeated but using 5-demethoxy-6-oxo-6-deoxy fumagillol (300 mg), to give 240 mg of the title compound as white solid.

$^1$H NMR (CDCl$_3$) : 5.18 (m, 1H), 3.18 (m, 2H), 2.87–1.68 (m, 10H), 2.08 (s, 3H), 1.88 (s, 3H), 1.74 (s, 3H), 1.41 (s, 3H)

EXAMPLE 20

2-(1,2-Epoxy-1,5-dimethyl-4-hexenyl)-1-dimethylsulfoniomethyl-4-oxo-1-cyclohexanol iodide The same procedure as Example 18 was repeated but using the compound (240 mg) of Example 19, to give 230 mg of the title compound as white solid.

$^1$H NMR (CDCl$_3$) : 5.18 (m, 1H), 3.18 (m, 2H), 2.87~1.68 (m, 10H), 2.08 (s, 6H), 1.88 (s, 3H), 1.74 (s, 3H), 1.41 (s, 3H)

Pharmaceutical Preparation Example

1. Preparation of Tablet

| Active ingredient | 5.0 mg |
|---|---|
| Lactose BP | 150.0 mg |
| Starch BP | 30.0 mg |
| Pregelatinized corn starch BP | 15.0 mg |
| Magnesium stearate | 1.0 mg |

Active ingredient was sieved, mixed with lactose, starch and pregelatinized corn starch. To the mixture, purified water was added. The paste was granulated, dried, mixed with magnesium stearate, and then compressed to obtain tablet.

2. Preparation of Capsule

| Active ingredient | 5.0 mg |
|---|---|
| Starch 1500 | 100.0 mg |
| Magnesium stearate BP | 1.0 mg |

Active ingredient was sieved, and mixed with additives. This mixture was filled in gelatin capsule to give the capsule.

3. Preparation of Injection

| Active ingredient | 100 g/ml |
|---|---|
| d-HCl | to be pH 3.5 |
| Saline for Injection BP | maximum 1 ml |

Active ingredient was dissolved in proper volume of saline for injection BP. The pH of the resultant solution was controlled with d-HCl BP to be pH 3.5, and then its volume was controlled with saline for Injection BP. The solution mixed completely was filled in 5-ml type 1 ample maken of glass. The top of ample was fused for sealing. The solution contained in ample was autoclaved at 120 for 15 min to be sterilized and to obtain an injection.

Examination of the Inhibiting Activity on Angiogenesis (In Vitro)

The compound sample dissolved in DMSO was diluted to ten times by using MEM culture medium (in case of CPAE cells) without adding FBS (Fetal Bovine Serum) and RPMI 1640 culture (in case of EL-4 and P388D1 cells), and 20 of the solution was poured to each well of 96 well plate in triplicate for every concentration gradient. Then, each cell suspension was prepared and poured to examine the inhibiting activity on angiogenesis.

In case of CPAE (Calf Pulmonary Artery Endothelial) cells (used after 2–3 subcultures), a cell suspension having 7×10³ cells/ml was prepared with MEM (+10% FBS+50 μg/ml ECGS) medium, and after pouring the suspension (180 μl) to each well of 96 well plate, they were cultured in a $CO_2$ incubator (5% $CO_2$, humidified) for 4 days. The inhibiting activity on angiogenesis was measured by means of SRB method, and the results are shown in Table 1.

In case of EL-4 (Lymphoma, murine) and P388D1 (leukemia, mouse) cells, a cell suspension having 1×10⁴ cells/ml was prepared with RPMI1640 (+10% FBS) culture medium, and after pouring the suspension (180 μl) to each well of 96 well plate, they were cultured in a $CO_2$ incubator (5% $CO_2$, humidified) for 3 days. The inhibiting activity on angiogenesis was measured by means of MTT method, and the results are shown in Table 1.

TABLE 1

The result of IC50 (g/ml)

| The compound | Cell lines | | |
|---|---|---|---|
| | CPAE | EL-4 | P388 |
| Fumagillin | $3.2 \times 10^{-3}$ | $1.6 \times 10^{-3}$ | ≧10 |
| 5-Demethoxy fumagillin | $2.8 \times 10^{-2}$ | $2.1 \times 10^{-2}$ | ≧10 |
| Compound of Example 4 | $5.7 \times 10^{-4}$ | $4.6 \times 10^{-4}$ | ≧10 |
| Compound of Example 5 | $2.8 \times 10^{-4}$ | $5.2 \times 10^{-4}$ | ≧10 |
| Compound of Example 7 | $4.2 \times 10^{-5}$ | $6.6 \times 10^{-5}$ | ≧10 |
| Compound of Example 8 | $3.2 \times 10^{-4}$ | $2.6 \times 10^{-4}$ | ≧10 |
| Compound of Example 9 | $3.6 \times 10^{-4}$ | $4.3 \times 10^{-4}$ | ≧10 |
| Compound of Example 10 | $4.6 \times 10^{-4}$ | $8.2 \times 10^{-4}$ | ≧10 |
| Compound of Example 11 | $1.2 \times 10^{-5}$ | $4.1 \times 10^{-5}$ | ≧10 |
| Compound of Example 14 | $1.9 \times 10^{-4}$ | $4.1 \times 10^{-4}$ | ≧10 |
| Compound of Example 20 | $1.2 \times 10^{-5}$ | $3.2 \times 10^{-5}$ | ≧10 |

As can be seen from the results of Table 1, the compounds according to the present invention and salts thereof strongly restrains Industrial Applicability Thus, the compounds of Chemical Formula 1 according to the present invention and salts thereof can be used as an angiogenesis inhibitor.

We claim:

1. A compound, or a pharmaceutically acceptable salt thereof, represented by Formula 1:

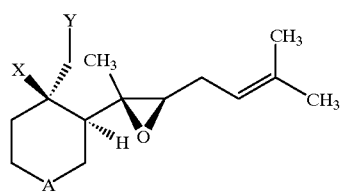

wherein
a) —X is —OH; and
—Y is chosen from halogen and,

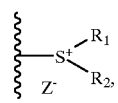

wherein
$R_1$ and $R_2$ are individually chosen from —H and substituted or unsubstituted lower alkyl, with the proviso that $R_1$ and $R_2$ are not both —H; and
$Z^-$ is a counter ion; or —X and —Y taken together form an oxirane ring; and b) —A— is chosen from

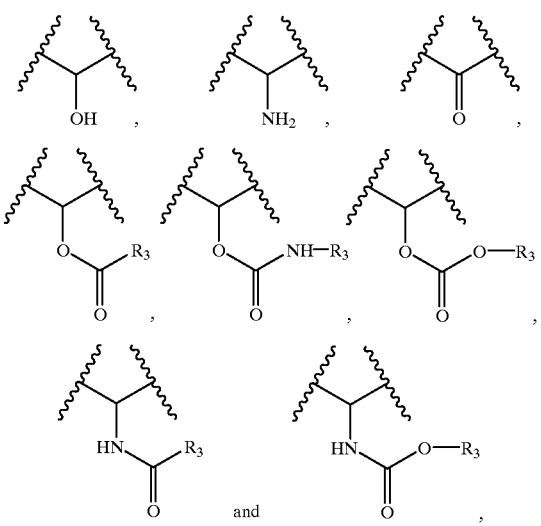

wherein
$R_3$ is chosen from substituted or unsubstituted lower alkyl, substituted or unsubstituted alkanoyl, substituted or unsubstituted aryl, substituted or unsubstituted arylalkyl and arylalkanoyl.

2. A compound, or a pharmaceutically acceptable salt thereof, according to claim 1, wherein:
—A— is chosen from

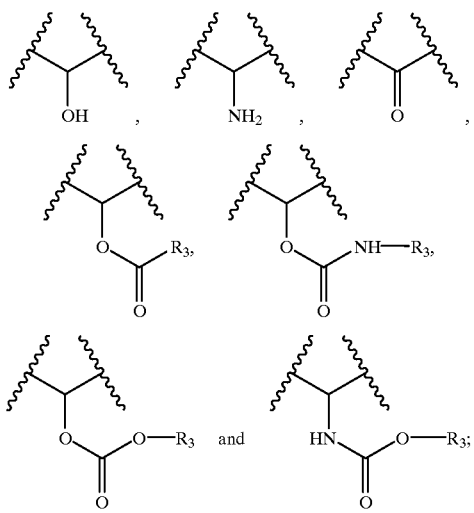

and
$R_3$ is chosen from substituted or unsubstituted lower alkyl, substituted or unsubstituted alkanoyl, substituted or unsubstituted aryl and substituted or unsubstituted arylalkyl.

3. A compound according to claim 1, selected from the group consisting of:
5-demethoxy-6-oxo-6-deoxyfumagillol,
5-demethoxyfumagillol,
3-chloromethyl-5-demethoxy-3-hydroxy-6-oxo-6-deoxyfumagillol,
5-demethoxy-6-O-cinnamoylfumagillol,
5-demethoxy-6-O-(3,4,5-trimethoxy)cinnamoyl fumagillol, 5-demethoxy-6-O-(4-chlorocinnamoyl)fumagillol,
4-O-chloroacetylcarbamoyl-1-chloromethyl-1-cyclohexanol,
5-demethoxy-6-O-[3-(4-methoxyphenyl)propionyl]fumagillol,
O-benzyloxycarbonyl-5-demethoxyfumagillol,
6-amino-5-demethoxy-6-deoxyfumagillol,
6-(4-methoxycinnamoyl)amino-5-demethoxy-6-deoxyfumagillol,
6-(4-dimethylaminocinnamoyl)amino-5-demethoxy-6-deoxyfumagillol,
6-[3-(4-methoxyphenyl)propionyl]amino-6-deoxy-5-demethoxyfumagillol,
2-(1,2-epoxy-1,5-dimethyl-4-hexenyl)-1-methylthiomethyl-1,4-cyclohexanediol,
4-O-(chloroacetylcarbamoyl)-2-(1,2-epoxy-1,5-dimethyl-4-hexenyl)-1-methylthiomethyl-1-cyclohexanol,
4-O-(chloroacetylcarbamoyl)-2-(1,2-epoxy-1,5-dimethyl-4-hexenyl)-1-dimethylsulfoniomethyl-1-cyclohexanol iodide,
2-(1,2-epoxy-1,5-dimethyl-4-hexenyl)-1-methylthiomethyl-4-oxo-1-cyclohexanol, and
2-(1,2-epoxy-1,5-dimethyl-4-hexenyl)-1-dimethylsulfoniomethyl-4-oxo-1-cyclohexanol iodide.

4. A process for preparing 5-demethoxyfumagillol 2, said process comprising:

a) demethoxylating compound 19 to obtain compound 6; and

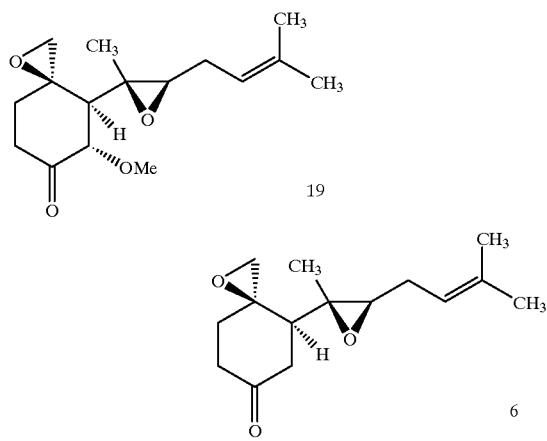

b) reducing compound 6 to obtain 5-demethoxyfumagillol 2.

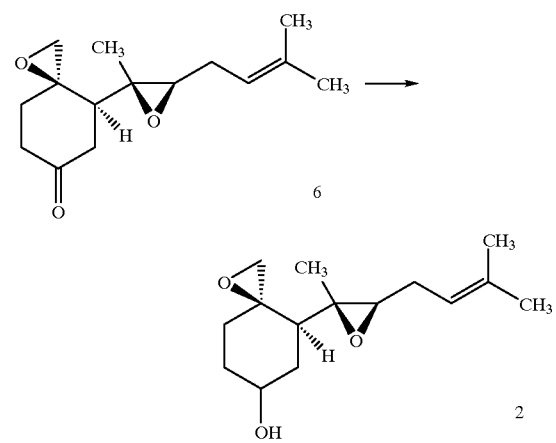

5. 5-Demethoxyfumagillin represented by Chemical Formula 17.

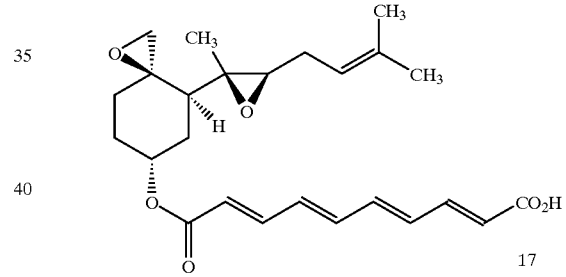

6. A composition for inhibiting angiogenesis in a mammal, said composition comprising a therapeutically effective amount of a compound, or a pharmaceutically acceptable salt thereof, according to claim 1, and a pharmaceutically acceptable carrier.

* * * * *

UNITED STATES PATENT AND TRADEMARK OFFICE
CERTIFICATE OF CORRECTION

PATENT NO. : 6,040,337
DATED : March 21, 2000
INVENTOR(S) : Hong, II et al.

It is certified that error appears in the above-indentified patent and that said Letters Patent is hereby corrected as shown below:

ON THE TITLE PAGE:

After Item [19], delete "Hong, II et al." and replace with --Hong et al.--

Item [75] Inventors:

Line 1, delete "Chung Hong, II" and replace with --Chung Il Hong--.
Line 10, delete "Kyunggi," and replace with --Kyunggi-do,--.

Signed and Sealed this

Thirteenth Day of March, 2001

*Attest:*

NICHOLAS P. GODICI

*Attesting Officer*   *Acting Director of the United States Patent and Trademark Office*